United States Patent [19]

Chan

[11] Patent Number: 4,648,897

[45] Date of Patent: Mar. 10, 1987

[54] HERBICIDAL N-OXADIAZOLYLMETHYL-, N-THIADIAZOLYLMETHYL-, AND N-TRIAZOLYLMETHYL-SUBSTITUTED ALPHA-HALOACETANILIDE

[75] Inventor: David C. K. Chan, Petaluma, Calif.

[73] Assignee: Chevron Research Company, San Francisco, Calif.

[21] Appl. No.: 170,482

[22] Filed: Jul. 21, 1980

Related U.S. Application Data

[62] Division of Ser. No. 904,955, May 11, 1978, Pat. No. 4,243,408.

[51] Int. Cl.⁴ .................. C07D 249/08; C07D 271/10; C07D 285/12; A01N 43/82
[52] U.S. Cl. .......................................... 71/90; 71/92; 71/88; 548/136; 548/138; 548/142; 548/143; 548/144; 548/262
[58] Field of Search .................. 71/90, 92; 548/136, 548/138, 142, 143, 144, 262

[56] References Cited

U.S. PATENT DOCUMENTS 4,221,584  9/1980  Ziman ..................................... 71/88

FOREIGN PATENT DOCUMENTS 2805757  8/1979  Fed. Rep. of Germany .......... 71/92

Primary Examiner—Glennon H. Hollrah
Assistant Examiner—D. L. Dinner
Attorney, Agent, or Firm—S. R. LaPaglia; T. G. DeJonghe; L. S. Squires

[57] ABSTRACT

Compounds of the formula

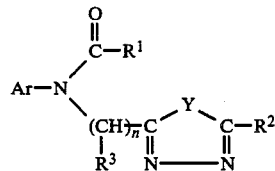

wherein Ar is aryl, $R^1$ is halomethyl, $R^2$ is hydrogen, alkyl, alkenyl, alkynyl, cycloalkyl, alkoxy, haloalkyl, alkylthio, alkenylthio, alkynylthio, aryl or $NR^5R^6$ wherein $R^5$ and $R^6$ individually are hydrogen, alkyl, alkenyl or alkynyl, $R^3$ is hydrogen or alkyl, n is 1 or 2, Y is O, S or NR wherein R is hydrogen, alkyl, alkenyl or alkynyl, have been found to be useful herbicides. The compounds are prepared by acylation of the corresponding N-heterocyclealkylene-N-arylamine.

27 Claims, No Drawings

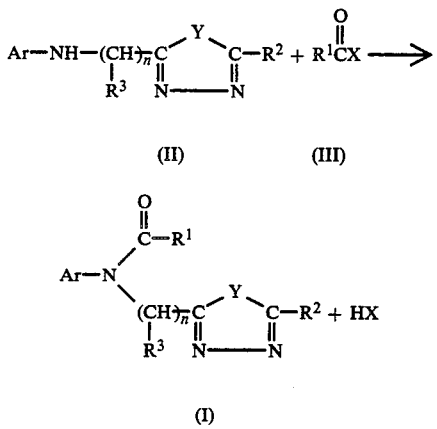

(I)

wherein Ar, $R^1$, $R^2$, $R^3$, Y and n have the same meaning as previously defined, and X is chloro or bromo.

The acylation reaction (1) is conducted by conventional procedures, preferably in the presence of an organic amine such as a trialkyl amine or a pyridine compound to scavenge the hydrogen halide by-product. The reactants (II) and (III) and the amine are generally contacted in substantially equimolar amounts in an inert organic solvent at a temperature of 0° to 100° C. Suitable inert organic solvents include ethyl acetate, dichloromethane, dimethoxyethane, benzene, etc. The product (I) is isolated and purified by conventional procedues such as extraction, distillation, chromatography, crystallization, etc.

The oxadiazole intermediate of formula (II) (Y=O) is prepared by the cyclization reaction of a hydrazide (IV) and an imidate.hydrochloride (V) under basic reaction conditions, as depicted in the following reaction (2):

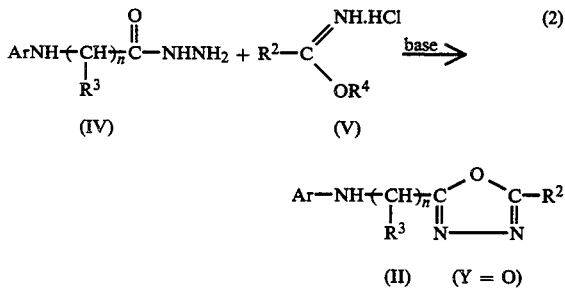

wherein $R^2$, $R^3$, Ar and n have the same meaning as previously defined, and $R^4$ is lower alkyl of 1 to 3 carbon atoms.

Generally, reaction (2) is conducted by reacting substantially equimolar amounts of the hydrazide (IV), the imidate (V) and an organic base, such as pyridine compound, in the liquid phase at a temperature of 25° to 150° C. In one modification of the reaction, excess of the organic base, i.e., pyridine, is used as solvent. Other suitable organic solvents for the reaction include chlorinated hydrocarbons, e.g., dichloromethane, and aromatic compounds, e.g., toluene and chlorobenzene. The product is isolated and purified by conventional procedures such as extraction, distillation, chromatography, crystallization, etc.

The triazole intermediate of formula (II) (Y=NH) is prepared by the cyclization reaction of a hydrazide (IV) and an amidine (VI) under basic reaction conditions, as depicted in reaction (3):

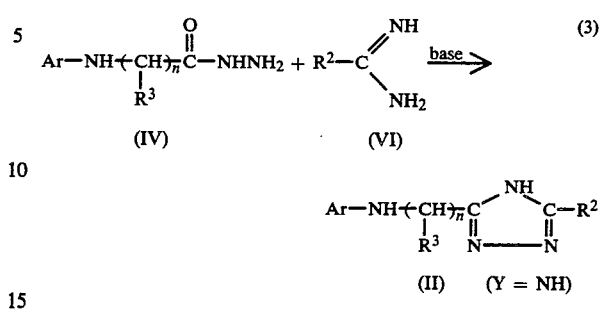

wherein $R^2$, $R^3$, Ar and n have the same meaning as previously defined. It is appreciated, of course, that the triazole ring of formula (II) may exist in other tautomeric forms.

The cyclization reaction (3) is conducted in the presence of a base. Suitable bases are inorganic alkali metal hydroxdes such as sodium hydroxide and potassium hydroxide. Generally, substantially molar amounts of reactants (IV) and (VI) and the base are employed. Preferably, however, a small excess of the base is employed, e.g., the molar ratio of base to hydrazide is preferably from 1.2:1 to 1.1:1. The reaction is conducted in the liquid phase in organic solvents. When an inorganic alkali metal hydroxide is employed as the base, alkanols, e.g., methanol, in which the hydroxide is partially soluble are preferably employed as the solvent. Reaction temperatures generally vary from 25° C. to 150° C. The product (II) is generally purified by conventional procedures, e.g., extraction, distillation or crystallization, before use in the acylation reaction (1).

The triazole intermediates of formula (II) (Y=NH) may also be prepared by the reaction of the hydrazide (IV) and the imidate (V) in the liquid phase under neutral reaction conditions as depicted in reaction (4):

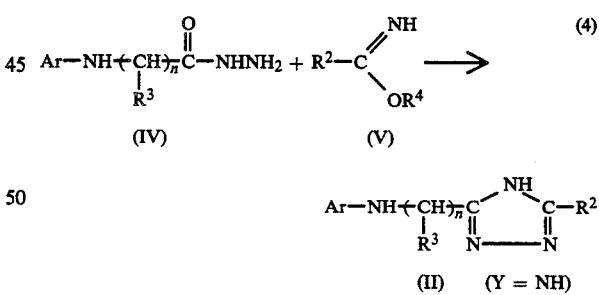

wherein $R^2$, $R^3$, $R^4$, Ar and n have the same significance as previously defined.

Reaction (4) is carried out under substantially the same reaction conditions as reaction (2), except no base is employed. For example, generally substantially equimolar amounts of the reactants (IV) and (V) are reacted in an inert organic solvent at a temperature of from 25° C. to 150° C., preferably 50° C. to 150° C.

The hydrazide intermediate (IV) is prepared by reacting an anilino-ester compound of formula (VII) or an anilino-thioester compound of formula (VIII) with hydrazine by conventional procedures, as depicted below:

HERBICIDAL N-OXADIAZOLYLMETHYL-, N-THIADIAZOLYLMETHYL-, AND N-TRIAZOLYLMETHYL-SUBSTITUTED ALPHA-HALOACETANILIDE

This is a division of application Ser. No. 904,955, filed May 11, 1978 now U.S. Pat. No. 4,243,408.

DESCRIPTION OF THE PRIOR ART

U.S. Pat. No. 3,901,917, issued Aug. 26, 1975 to S. B. Richter, discloses herbicidal N-thienylalkylacetanilides.

U.S. Pat. No. 3,819,661, issued June 25, 1974 to L. L. Maravetz, discloses herbicidal 2-chloro-N-furfuryl or tetrahydrofurfurylacetanilides.

U.S. Pat. No. 3,907,544, issued Sept. 23, 1975 to J. F. Olin, discloses herbicidal 2-halo-N-(cyclicimidoalkylene)-substituted acetanilides.

U.S. Pat. Nos. 3,859,308, 3,888,882 and 3,946,046, issued to S. B. Richter, disclose N-alpha-haloacetyl-N-(1,3-dioxan-2-ylalkyl)anilides.

DESCRIPTION OF THE INVENTION

The compounds of the invention are represented by the formulas

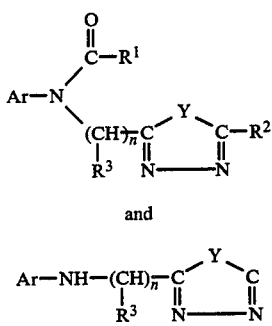

wherein Ar is phenyl or phenyl substituted with 1 to 3 of the same or different substituents selected from fluoro, chloro, bromo, iodo, alkyl of 1 to 4 carbon atoms, alkoxy of 1 to 4 carbon atoms or haloalkyl of 1 to 4 carbon atoms and 1 to 3 of the same or different halogens selected from fluoro, chloro, bromo or iodo, $R^1$ is halomethyl of 1 to 3 of the same or different halogens selected from fluoro, chloro, bromo, or iodo, $R^2$ is hydrogen; alkyl of 1 to 6 carbon atoms; alkenyl of 2 to 6 carbon atoms; alkynyl of 2 to 6 carbon atoms; cycloalkyl of 3 to 6 carbon atoms; haloalkyl of 1 to 4 carbon atoms and 1 to 3 of the same or different halogens selected from fluoro, chloro, bromo or iodo; alkoxy of 1 to 6 carbon atoms; alkylthio of 1 to 6 carbon atoms; alkenylthio of 2 to 6 carbon atoms; alkynylthio of 2 to 6 carbon atoms; phenyl; phenyl substituted with 1 to 3 of the same or different substituents selected from fluoro, chloro, bromo, iodo, alkyl of 1 to 4 carbon atoms, alkoxy of 1 to 4 carbon atoms or haloalkyl of 1 to 4 carbon atoms and of 1 to 3 of the same or different halogens selected from fluoro, chloro, bromo or iodo; or $NR^5R^6$ wherein $R^5$ and $R^6$ individually are hydrogen, alkyl of 1 to 6 carbon atoms, alkenyl of 2 to 6 carbon atoms or alkynyl of 2 to 6 carbon atoms, $R^3$ is hydrogen or alkyl of 1 to 6 carbon atoms, n is 1 or 2, and Y is O, S or NR wherein R is hydrogen, alkyl of 1 to 6 carbon atoms, alkenyl of 2 to 6 carbon atoms or alkynyl of 2 to 6 carbon atoms.

Representative substituted-phenyl groups which Ar and $R^2$ may represent are 2-fluorophenyl, 2,4-dichlorophenyl, 3,5-dibromophenyl, 4-iodophenyl, 4-methylphenyl, 2,6-diethylphenyl, 4-trifluoromethylphenyl, 2-methoxyphenyl, 2,6-dimethyl-4-chlorophenyl, 2,3,5-trimethylphenyl, 2,3,5,6-tetramethylphenyl. Preferred substituted-phenyl Ar groups are phenyl substituted with 1 to 2 of the same or different substituents selected from fluoro, chloro, bromo, alkyl of 1 to 4 carbon atoms or alkoxy of 1 to 4 carbon atoms.

Representative halomethyl groups which $R^1$ may represent include fluoromethyl, chloromethyl, bromomethyl, iodomethyl, dichloromethyl, tribromomethyl and fluorodichloromethyl.

Representative alkyl R, $R^2$, $R^3$, $R^5$ and $R^6$ groups are methyl, ethyl, isopropyl and n-hexyl.

Representative alkenyl R, $R^2$, $R^5$ and $R^6$ groups include vinyl, allyl, 2-butenyl and 3-hexenyl. Representative alkynyl R, $R^2$, $R^5$ and $R^6$ groups are propargyl, 2-butynyl, 1-butynyl and 5-hexynyl. Representative cycloalkyl $R^2$ groups are cyclopropyl, 2-methylcyclopentyl and cyclohexyl. Representative haloalkyl $R^2$ groups are chloromethyl, 3-bromopropyl, 2,2-dichloroethyl and trichloromethyl. Representative alkylthio, alkenylthio, alkynylthio $R^2$ groups are methylthio, ethylthio, isopropylthio, vinylthio, allylthio and propargylthio. Representative alkoxy $R^2$ groups are methoxy, ethoxy and n-propoxy.

Representative NR groups are amino, alkylamino, alkenylamino and alkynylamino such as methylamino, ethylamino, isopropylamino, n-hexylamino, allylamino, propargylamino, etc. Representative $NR^5R^6$ groups are amino, methylamino, allylamino, propargylamino, dimethylamino, diethylamino, N-allyl-N-methylamino, etc.

Preferably Ar is phenyl substituted with 1 to 3 substituents selected from fluoro, chloro, bromo or alkyl of 1 to 3 carbon atoms. Most preferably Ar is phenyl substituted with substituents at the 2- and the 6-positions, especially 2,6-dialkylphenyl.

Preferably $R^1$ is monohalomethyl, especially chloromethyl or bromomethyl.

Preferably $R^2$ is hydrogen, alkyl of 1 to 3 carbon atoms, phenyl or phenyl substituted with 1 to 3 fluoro, chloro, bromo or alkyl of 1 to 3 carbon atoms. Most preferably $R^2$ is hydrogen or alkyl of 1 to 3 carbon atoms.

Preferably Y is O or NR wherein R is hydrogen or alkyl of 1 to 3 carbon atoms, and preferably n is 1.

A preferred class of compounds represented by formula (I) is that wherein Ar is 2,6-dialkylphenyl, $R^1$ is chloromethyl or bromomethyl, $R^2$ is hydrogen or alkyl of 1 to 6 carbon atoms, Y is oxygen and n is 1.

Another preferred class of compounds represented by formula (I) is that wherein Ar is 2,6-dialkylphenyl, $R^1$ is chloromethyl or bromomethyl, $R^2$ is hydrogen or alkyl of 1 to 6 carbon atoms, Y is NR wherein R is hydrogen, alkyl of 1 to 3 carbon atoms or alkenyl of 2 to 6 carbon atoms and n is 1. In this class, $R^2$ most preferably is alkyl and Y most preferably is NH.

The compounds of the invention are prepared by acylating an oxadiazole, thiadiazole or triazole (II) with an acyl halide (III), as depicted by the following reaction (1):

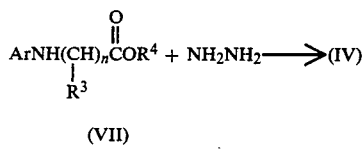

(VII)

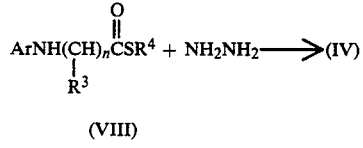

(VIII)

wherein $R^3$ and Ar have the same significance as previously defined.

The thiadiazole intermediate of formula (II) (Y=S) is prepared by the following sequence of reactions:

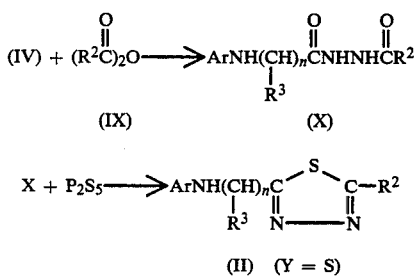

wherein Ar, $R^2$, $R^3$ and n have the same significance as previously defined.

Reaction (7) is conducted by reacting substantially equimolar amounts of the hydrazide (IV) and the anhydride (IX) in the liquid phase in an inert diluent at a temperature of about 25° C. to 100° C. Reaction (8) is conducted by reacting substantially equimolar amounts of the bis-acylated hydrazine (X) and phosphorus pentasulfide in the liquid phase in the inert diluent at a temperature of 50° C. to 150° C. Reaction (8) is preferably conducted in a basic organic solvent such as pyridine and methyl-substituted pyridines.

The triazole intermediates of formula (II) wherein $R^2$ is alkylthio, alkenylthio or alkynylthio are prepared by the following sequence of reactions:

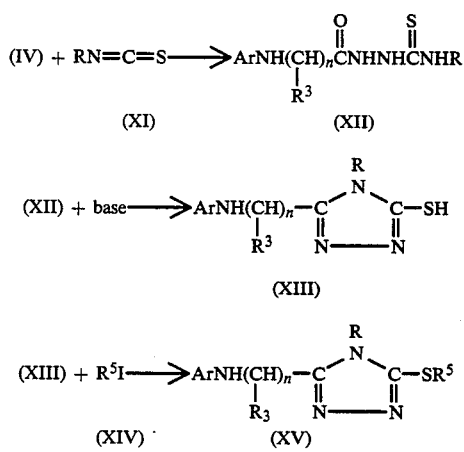

wherein $R^3$, $R^4$ and n have the same significance as previously defined, and R and $R^5$ are alkyl, alkenyl or alkynyl as previously defined.

Reaction (9) comprises reacting a hydrazide (IV) and an isothiocyanate (XI) to form the semithiocarbazide (XII) by conventional procedures. Reaction (10) comprises the cyclization of the semithiocarbazide (XII) in the presence of a base. Reaction (10) is generally conducted by reacting substantially equimolar amounts of the semithiocarbazide (XII) and a strong inorganic base, e.g., alkali metal hydroxides such as sodium hydroxide or potassium hydroxide, in an alkanol reaction medium, e.g., methanol or ethanol, at a temperature of 50° C. to 100° C. Reaction (11) comprises the alkylation of the mercapto-substituted triazole product (XIII) with the iodo compound (XIV) by conventional procedures.

The oxadiazole intermediates of formula (II) wherein $R^2$ is alkylthio, alkenylthio or alkynylthio are prepared by the following reaction:

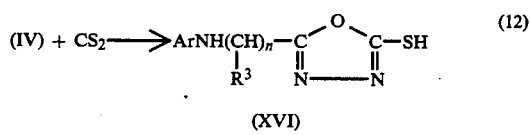

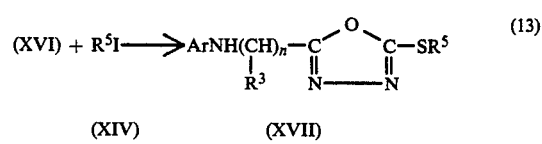

wherein $R^3$ and n have the same significance as previously defined, and $R^5$ is alkyl, alkenyl or alkynyl as previously defined.

Reaction (12) comprises the cyclization of the hydrazide (IV) with carbon disulfide in the presence of a base to give the mercapto-substituted oxadiazole (XVI). Reaction (13) comprises the alkylation of the mercapto-substituted oxadiazole (XVI) with the iodoalkane (XIV) by conventional procedures. Reaction (12) is generally conducted by reacting substantially equimolar amounts of the hydrazide (IV), carbon disulfide and a strong inorganic base, e.g., alkali metal hydroxides, in an alkanol solvent, e.g., methanol or ethanol, at a temperature of 25° C. to 100° C. An excess of carbon disulfide can be used, if desired. For example, the molar ratio of hydrazide (IV) to carbon disulfide varies from 1.5:1 to 1:1.

The oxadiazole intermediate of formula (II) can also be prepared by the following reaction:

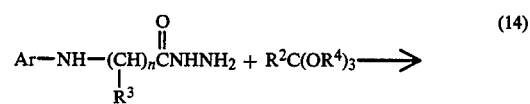

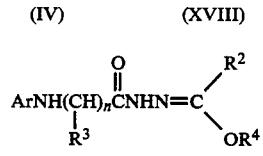

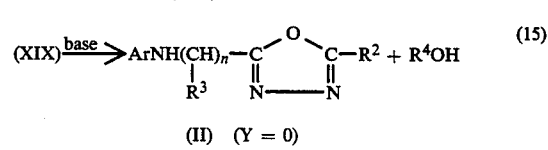

wherein Ar, $R^2$, $R^3$, $R^4$ and n have the same meaning as previously defined.

Reaction (14) comprises the reaction of the hydrazide (IV) with an ortho-ester (XVIII) in the liquid phase at elevated temperatures, e.g., 50°–200° C. Reaction (14) is conducted in a basic solvent, e.g., pyridine and alkylated-pyridines such as collidine and lutidine. Generally, the molar ratio of hydrazide (IV) to otho-ester (XVIII) is substantially equimolar, e.g., the molar ratio of hydrazide to ortho-ester varies from 1.2:1 to 1:1.2. In reaction (15), the imidate product (IX) is cyclized by heating in a basic organic solvent, e.g., trialkylamines and N,N-dialkylanilines at elevated temperatures, e.g., 100°–250° C. The oxadiazole product (II) is isolated and purified by conventional procedures.

EXAMPLES

Example 1

Preparation of alpha-(2,6-dimethylphenylamino)acethydrazide

A solution of 100 g (0.48 mol) methyl alpha-(N-2,6-dimethylphenylamino)thioacetate in 50 ml methanol was added dropwise to a stirred solution of 27 g (0.72 mol) hydrazine hydrate (85%) in 200 ml methanol at 25° C. The resulting reaction mixture was stirred at 25° C. for about 16 hours and then evaporated under reduced pressure at 46° C. to give an oil residue. The residue was dissolved in 500 ml dichloromethane, washed with 100 ml water and dried over magnesium sulfate. The dichloromethane was then removed by evaporation under reduced pressure and the resulting oil crystallized from ethyl ether to give the crude alpha-(2,6-dimethylphenylamino)acethydrazide. The crude acethydrazide product was washed successively with 100 ml portions of 50% ethyl ether in petroleum ether, 75% ethyl ether in petroleum ether, and ethyl ether and then air dried to give 65.5 g of purified product, m.p. 86°–88° C.

Example 2

Preparation of 2-(2,6-dimethylphenylaminomethyl)-5-methyl-1,3,4-oxadiazole)

A solution of 19.3 g (0.1 mol) alpha-(2,6-dimethylphenylamino)acethydrazide and 14 g (0.11 mol) ethyl actimidate hydrochloride (Aldrich Chemical Co.) in 150 ml pyridine was heated under reflux for 9 hours. The reaction mixture was filtered and the filtrate was evaporated under reduced pressure to give an oil. The oil was placed on 400 g silica gel in a chromatography column and eluted the following solvent systems: (1) petroleum ether, (2) petroleum ether/ethyl ether, (3) ethyl ether, and (4) ethyl ether/methanol. The crude product (11.5 g) was eluted from the column with the ethyl ether/methanol solvent system. Crystallization of the crude product from dichloromethane/ethyl ether gave 7.4 g of crystalline product, m.p. 134°–135° C. The product is tabulated in Table I as Compound No. 1-A.

Example 3

Preparation of N-(5-methyl-1,3,4-oxadiazol-2-ylmethyl)-2,6-dimethyl-alpha-chloroacetanilide A solution of 1.9 g (0.0166 mol) chloroacetyl chloride in ethyl acetate was added dropwise to a stirred solution of 3.6 g (0.0166 mol) 2-((2,6-dimethylphenylaminomethyl)-5-methyl-1,3,4-oxadiazole and 1.3 g (0.0166 mol) pyridine in 100 ml ethyl acetate at 25° C. The resulting reaction mixture was stirred at 25° C. for 18 hours. Thin-layer chromatography showed the presence of small amounts of unreacted 2-(2,6-dimethylphenylaminomethyl)-5-methyl-1,3,4-oxadiazole in the reaction mixture. An 0.3-g sample of pyridine and 0.4 g sample chloroacetyl chloride were then added to the reaction mixture. The reaction mixture was stirred another 3 hours at 25° C. and diluted with 100 ml water. The organic layer was separated, washed with water, saturated aqueous sodium bicarbonate, dried over magnesium sulfate and evaporated under reduced pressure to give a solid. The solid was washed with ethyl ether/petroleum ether at 0° C. and dried to give 3.7 g of colorless product, m.p. 109°–111° C. The product and its elemental analysis are tabulated in Table I, as Compound No. 1-B.

Example 4

Preparation of 3-(2,6-dimethylphenylaminomethyl)-5-methyl-1,2,4-triazole

To a stirred solution of 8.8 g (0.022 mol) sodium hydroxide in 500 ml methanol was added 20 g (0.22 mol) acetamidine hydrochloride. After stirring for an additional ¼ hour, 37.7 g (0.2 mol) alpha-(2,6-dimethylphenylamino)acethydrazide was added. The reaction mixture was heated under reflux for about 18 hours, cooled and filtered. The filtrate was evaporated under a reduced pressure to give a solid residue. The residue was diluted with dichloromethane, filtered, dried over magnesium sulfate and evaporated under reduced pressure to give a solid residue, which was triturated with ethyl ether/petroleum ether and dried to give 34.3 g of the product, m.p. 125°–126° C. The product is tabulated in Table I as Compound No. 2-A.

Example 5

Preparation of N-(5-methyl-1,2,4-triazol-3-ylmethyl)-2,6-dimethyl-alpha-chloroacetanilide A solution of 5 g (0.044 mol) chloroacetyl chloride in 2 ml toluene was added dropwise over a one-hour period to a stirred solution of 8.7 g (0.04 mol) 3-(2,6-dimethylphenylaminomethyl)-5-methyl-1,2,4-triazole and 4.5 g (0.044 mol) triethylamine at 78°–96° C. The resulting reaction mixture was maintained at 80°–85° C. for another 3 hours and then allowed to cool to about 25° C. overnight. The reaction mixture was diluted with water. The precipitated product was filtered, washed with water and dissolved in dichloromethane. The dichloromethane solution was dried over magnesium sulfate, treated with charcoal, filtered and evaporated under reduced pressure to give a colorless solid. Trituration of the solid with cold ethyl ether gave 5.1 g of the product, as a colorless solid, m.p. 178°–179° C. The product and its elemental analysis are tabulated in Table I, as Compound No. 2B.

Example 6

Preparation of 1-[alpha-(2,6-dimethylphenylamino)acetyl]-4-methyl-semithiocarbazide A solution of 24.8 g (0.339 mol) methyl isothiocyanate in 75 ml dichloromethane was added dropwise to a solution of 65.5 g (0.339 mol) alpha-(2,6-dimethylphenylamino)acetic acid hydrazide in 450 ml dichloromethane over a period of 1.25 hours at about 25° C. The reaction mixture was heated under reflux for one hour, during which time the product precipitated. The reaction mixture was cooled, and the product filtered, washed successively with dichloromethane and diethylether, and dried in vacuuo at 40°–50° C. The product melted at 173°–174° C. Elemental analysis for $C_{12}H_{18}N_4OS$ showed:

|     | Calc. | Found |
| --- | --- | --- |
| % C | 54.1 | 52.6 |
| % H | 6.8 | 6.9 |
| % N | 21.0 | 20.5 |

Example 7

Preparation of 3-(2,6-dimethylphenylaminomethyl)-4-methyl-5-mercapto-1,2,4-triazole To a stirred hot solution of 52.8 g (0.198 mol) 1-[alpha-(2,6-dimethylphenylamino)acetyl]-4-methylthiosemicarbazide in 560 ml ethanol was added quickly 8 g (0.198 mol) sodium hydroxide. The reaction mixture was heated under reflux for 2 hours and allowed to stand overnight. The ethanol was then evaporated under reduced pressure to give a solid residue. Water (500 ml) was added to the solid residue and the resulting aqueous mixture was filtered to remove a small amount of a solid. The filtrate was neutralized with concentrated hydrochloric acid, the colorless solid was filtered, washed with water and partially dried in vacuuo over potassium hydroxide pellets at 50° C. The nearly dried product was dissolved in dichloromethane and the aqueous layer separated. The organic layer was dried over magnesium sulfate, filtered and evaporated under reduced pressure to give 43.5 g of the product as a colorless solid, m.p. 172°–173° C. The product is tabulated in Table I as Compound No. 3.

Example 8

Preparation of (3-(2,6-dimethylphenylaminomethyl)-4-methyl-5-methylthio-1,2,4-triazole To a stirred solution of 1.7 g (0.0419 mol) sodium hydroxide in 125 ml water was added in one portion, 10.4 g (0.0419 mol), 3-(2,6-dimethylphenylaminomethyl)-4-methyl-5-mercapto-1,2,4-triazole. After a homogeneous solution was obtained, 6.2 g (0.044 mol) methyl iodide was added dropwise. The reaction mixture was then diluted with 50 ml dichloromethane and vigorously stirred for 0.5 hour. The reaction mixture was diluted with another 100 ml dichloromethane and the organic layer was separated, dried over magnesium sulfate, filtered and evaporated under reduced pressure to give a solid residue. The solid was triturated with ethyl ether to give the product as a colorless solid. The product is tabulated in Table I as Compound No. 14-A.

Example 9

Preparation of 3-(N-chloroacetyl-2,6-dimethylphenylamino)-4-methyl-5-methylthio-1,2,4-triazole To a stirred solution of 6.1 g (0.0232 mol) 3-(2,6-dimethylphenylamino)-4-methyl-5-methylthio-1,2,4-triazole in 150 ml toluene was added quickly 2.7 g (0.024 mol) chloroacetyl chloride. An exotherm ensued and the temperature rose to 100° C., followed by separation of an oil which solidified. The reaction mixture was stirred at 100°–105° C. for 1 hour, cooled and diluted with 50 ml saturated sodium bicarbonate and 20 ml dichloromethane. The clear organic layer was separated, dried over magnesium sulfate and evaporated under reduced pressure to give a clear oil. The oil was crystallized from ethyl ether to give 7.4 g of product, as a pale yellow solid, m.p. 145°–147° C. The product is tabulated in Table I as Compound No. 14-B.

Example 10

Preparation of 2-(2,6-dimethylphenylaminomethyl)-5-methyl-1,3,4-thiadiazole

To a stirred solution of 19.9 g (0.103 mol) alpha-(2,6-dimethylphenylamino)acethydrazide in 350 ml dichloromethane was added quickly 11.3 g (0.103 mol) acetic anhydride. A mild exotherm ensued. After being stirred at about 25° C. for about 16 hours, the reaction mixture was filtered to give 8.9 g of 1-(2,6-dimethylphenylaminoacetyl)-2-acetyl hydrazine, m.p. 148°–150° C.

To a stirred solution of 16.0 g (0.068 mol) 1-(2,6-dimethylphenylaminoacetyl)-2-acetylhydrazine in 150 ml pyridine was added 15.1 g (0.068 mol) phosphorus pentasulfide in small portions. A mild exotherm ensued. The reaction mixture was heated to 140°–150° C. when an exotherm ensued. The reaction temperature rose to 170° C., and then subsided. Hydrogen sulfide was liberated. The reaction was kept at 140°–150° C. for 2 hours and then at 25° C. for about 16 hours. The pyridine solution was decanted from a gummy brown residue. The residue was extracted with dichloromethane. The dichloromethane extracts were combined with the pyridine solution and evaporated under reduced pressure to give an oil. The oil was dissolved in dichloromethane and treated with ice water to destroy a small amount of unreacted phosphorus pentasulfide. The dichloromethane solution was then washed with cold dilute aqueous sodium hydroxide solution, water, dried over magnesium sulfate, filtered and evaporated under reduced pressure at 40°–50° C. to give an oil. The oil was column chromatographed on 200 g silica gel using petroleum ether/diethyl ether as eluants. The major fractions were combined in dichloromethane, dried over magnesium sulfate, filtered and evaporated under reduced pressure to give a clear oil which crystallized upon trituration with petroleum ether to give 11.6 g of 2-(2,6-dimethylphenylaminomethyl)-5-methyl-1,3,4-thiadiazole, m.p. 68°–69° C. The product is tabulated in Table I as Compound No. 29A.

Example 11

Preparation of N-(5-methyl-1,3,4-thiadiazol-2-yl-methyl)-2,6-dimethyl-alpha-chloroacetanilide To a stirred solution of 4 g (0.0171 mol) 2-(2,6-dimethylphenylaminomethyl)-5-methyl-1,3,4-thiadiazole and 1.4 g (0.018 mol) pyridine in 100 ml benzene heated to 85° C. was added quickly 2.0 g (0.018 mol) chloroacetyl chloride. A mild exotherm ensued, accompanied by separation of a solid. The reaction mixture was kept at 90°–95° C. for 2 hours, cooled and diluted with water. The organic layer was separated, washed with aqueous sodium bicarbonate solution, dried over magnesium sulfate, filtered and evaporated under reduced pressure to give an oil, which crystallized to give 3.9 g of the product, as a colorless crystalline solid, m.p. 117°–118°

C. The product is tabulated in Table I as Compound No. 29-B.

Example 12

Preparation of 2-(2,6-dimethlyphenylaminomethyl)-5-mercapto-1,3,4-oxadiazole

A 58.0-g (0.3 mol) sample of alpha-(2,6-dimethylphenylamino)acethydrazide was added to a solution of 19.8 g (0.3 mol) potassium hydroxide in 500 ml ethanol. A solution of 26.3 g (0.34 mol) carbon disulfide in 30 ml ethanol was added dropwise over a 45-minute period. A mild exotherm ensued, followed by the separation of a solid. After the addition was completed, the reaction mixture was diluted with ethanol and heated under reflux for about 14 hours until hydrogen sulfide evolution ceased. The reaction mixture was then cooled and filtered to remove an unidentified solid by-product. The filtrate was evaporated under reduced pressure at 46° C. to give an oil. The oil was dissolved in dichloromethane, extracted successively with water, aqueous sodium hydroxide solution and water. The aqueous extracts were combined, cooled to 0° C. and acidified with concentrated hydrochloric acid, causing a solid to crystallize. The solid was filtered, washed with water, dissolved in dichloromethane, dried over magnesium sulfate, filtered and evaporated under reduced pressure to give a solid residue. Trituration with ethyl ether/petroleum ether at 0° C. gave the product as a pale yellow powder, m.p. 115°–117° C.

Example 13

Preparation of 2-(2,6-dimethylphenylaminomethyl)-5-methylthio-1,3,4-oxadiazole

To a stirred mixture of 16.2 g (0.0688 mol) 2-(2,6-dimethylphenylaminomethyl)-5-mercapto-1,3,4-oxadiazole in 200 ml water and 200 ml dichloromethane was added quickly 2.8 g (0.0688 mol) sodium hydroxide. To the resulting reaction mixture was then added 9.9 g (0.0688 mol) iodomethane. The reaction mixture was stirred at about 25° C. for 1 hour and then heated under reflux for 1 hour. After the reaction mixture was allowed to stand overnight at 25° C., the organic layer was separated, dried over magnesium sulfate, filtered and evaporated under reduced pressure to give a yellow solid. Trituration with ethyl ether/petroleum ether gave 8.8 g of 2-(2,6-dimethylphenylaminomethyl)-5-methylthio-1,3,4-oxadiazole, m.p. 84°–85° C. The product is tabulated in Table I as Compound No. 24-A.

Chloroacetylation of the product gave N-(5-methylthio-1,3,4-oxathiazol-2-yl-methyl)-2,6-dimethyl-alpha-chloroacetanilide, which is tabulated in Table I as Compound No. 24-B.

Example 14

Preparation of 2-(2,6-dimethylphenylaminomethyl)-5-methyl-1,3,4-oxadiazole

A stirred solution of 11.0 g (0.05 mol) alpha-(2,6-diethylphenylamino)acethydrazide, 7.2 g (0.06 mol) trimethyl orthoacetate and 150 ml 2,6-dimethyllutidine was heated at 125°–130° C. for 16.5 hours and then at 150° C. for 22 hours. The reaction mixture was then evaporated under reduced pressure at 50°–60° C. to give an oil which crystallized to give a solid product, m.p. 109°–110°. Infrared (carbonyl at 1630 cm$^{-1}$) and nuclear magnetic analysis showed the following imidate structure for the product:

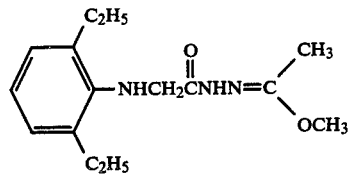

The imidate product was dissolved in 100 ml N,N-dimethylaniline and heated under a Dean Stark water separator at a temperature of 200°–240° C. for a period of 1.5 hours. Methanol was collected in the separator. The reaction mixture was allowed to cool to about 25° C., stirred overnight, and evaporated under reduced pressure at 62° C. to give an oil. The oil was chromatographed on silica gel (300 g). Elution with ethyl ether gave 10.3 g of the desired product as a colorless oil. Elemental analysis for $C_{14}H_{19}N_3O$ showed: %C, calc. 68.5, found 68.4; %H, calc. 7.8, found 7.9.

The compounds tabulated in Table I were prepared by procedures similar to those of Examples 1–14. The structure of each compound tabulated in Table I was confirmed by nuclear magnetic resonance and/or infrared spectroscopy.

UTILITY

The compounds of the present invention are, in general, herbicidal in both pre- and post-emergent applications. For pre-emergent control of undesirable vegetation, the herbicidal compounds will be applied in herbicidally effective amounts to the locus of growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. Some may be selective with respect to the type of application and/or type of weed.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g, hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 0.2 to 60 kg/ha, and the preferred rate is in the range 0.5 to 40 kg/ha.

Pre- and post-emergent herbicidal tests on representative compounds of the invention were made using the following methods:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 micrograms/cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) as a dose of 33 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

TABLE I

Compounds of the formula $$\text{Ar}-\text{N} \begin{array}{c} R^5 \\ \diagdown \\ (CH_2)_n\text{C}-\text{R}^3 \end{array} \begin{array}{c} Y \\ \diagdown \\ \parallel \\ N \end{array} \begin{array}{c} \\ \text{C}-R^2 \\ \parallel \\ N \end{array}$$

| No. | Ar | Y | R$^2$ | R$^3$ | n | R$^5$ | m.p., °C. | C Calc. | C Found | H Calc. | H Found | N(Cl) Calc. | N(Cl) Found |
|---|---|---|---|---|---|---|---|---|---|---|---|---|---|
| 1A | 2,6-(CH$_3$)$_2$φ | O | CH$_3$ | H | 1 | H | 134–135 | 66.3 | 66.9 | 7.0 | 7.2 | 19.3 | 21.1 |
| 1B | 2,6-(CH$_3$)$_2$φ | O | CH$_3$ | H | 1 | COCH$_2$Cl | 109–111 | | | | | (12.1) | (11.7) |
| 2A | 2,6-(CH$_3$)$_2$φ | NH | CH$_3$ | H | 1 | H | 125–126 | 66.6 | 66.5 | 7.5 | 7.5 | 25.9 | 25.7 |
| 2B | 2,5-(CH$_3$)$_2$φ | NH | CH$_3$ | H | 1 | COCH$_2$Cl | 178–179 | | | | | (12.11) | (12.2) |
| 3 | 2,6-(CH$_3$)$_2$φ | NCH$_3$ | SH | H | 1 | H | 172–173 | 58.0 | 57.5 | 6.5 | 6.6 | 22.6 | 22.6 |
| 4 | 2-CH$_3$—6-C$_2$H$_5$—φ | O | CH$_3$ | H | 1 | COCH$_2$Cl | 64–65 | | | | | (11.5) | (11.6) |
| 5A | 2,6-(C$_2$H$_5$)$_2$—φ | NH | CH$_3$ | H | 1 | H | 78–80 | 68.8 | 69.3 | 8.3 | 8.6 | 22.9 | 23.1 |
| 5B | 2,6-(C$_2$H$_5$)$_2$—φ | NH | CH$_3$ | H | 1 | COCH$_2$Cl | 170–171 | 59.9 | 60.1 | 5.6 | 6.6 | 17.5 | 18.5 |
| 6A | 2-CH$_3$—6-C$_2$H$_5$—φ | NH | CH$_3$ | H | 1 | H | 81–82 | 67.2 | 67.6 | 7.9 | 7.9 | 24.3 | 24.5 |
| 6B | 2-CH$_3$—6-C$_2$H$_5$—φ | NH | CH$_3$ | H | 1 | COCH$_2$Cl | 150–154 | 58.7 | 60.9 | 6.2 | 6.6 | 18.3 | 19.2 |
| 7A | 2-(CH$_3$)$_2$φ | NH | C$_2$H$_5$ | H | 1 | H | 93–95 | 67.8 | 67.7 | 7.9 | 8.0 | 24.3 | 24.0 |
| 7B | 2-(CH$_3$)$_2$φ | NH | C$_2$H$_5$ | H | 1 | COCH$_2$Cl | 137–141 | 58.7 | 58.8 | 6.2 | 6.3 | 18.3 | 18.5 |
| 8A | 2,6-(C$_2$H$_5$)$_2$—φ | NH | C$_2$H$_5$ | H | 1 | H | 55–60 | 69.8 | 67.2 | 8.6 | 8.4 | 21.7 | 21.2 |
| 8B | 2,6-(C$_2$H$_5$)$_2$—φ | NH | C$_2$H$_5$ | H | 1 | COCH$_2$Cl | 112–114 | 61.2 | 57.8 | 6.6 | 6.6 | 16.8 | 16.5 |
| 9A | 2,6-(CH$_3$)$_2$φ | NH | H | H | 1 | H | 149–151 | 65.3 | 62. | 7.0 | 6.8 | 22.7 | 25.3 |
| 9B | 2,6-(CH$_3$)$_2$φ | NH | H | H | 1 | COCH$_2$Cl | 172–174 | 56.1 | 54.9 | 5.4 | 5.5 | 20.1 | 19.4 |
| 10A | 2,6-(CH$_3$)$_2$φ | NH | CH$_3$ | H | 2 | H | 75–76 | 67.8 | 66.1 | 7.9 | 8.0 | 24.3 | 23.6 |
| 10B | 2,6-(CH$_3$)$_2$φ | NH | CH$_3$ | H | 2 | COCH$_2$Cl | 135–137 | 58.7 | 58.4 | 6.2 | 6.3 | 18.3 | 18.1 |
| 11A | 2,6-(CH$_3$)$_2$φ | NH | CH$_3$ | CH$_3$ | 1 | H | 106–108 | 67.7 | 68.8 | 7.9 | 8.1 | 24.3 | 24.8 |
| 11B | 2,6-(CH$_3$)$_2$φ | NH | CH$_3$ | CH$_3$ | 1 | COCH$_2$Cl | 138–139 | 58.7 | 58.9 | 6.2 | 6.4 | 18.4 | 18.4 |
| 12A | 2,6-(CH$_3$)$_2$φ | NH | H | CH$_3$ | 1 | H | 137–138 | 66.6 | 66.5 | 7.5 | 7.5 | 25.9 | 26.1 |
| 12B | 2,6-(CH$_3$)$_2$φ | NH | H | CH$_3$ | 1 | COCH$_2$Cl | 149–150 | 57.4 | 57.2 | 5.9 | 5.9 | 19.1 | 19.0 |
| 13 | 2,6-(CH$_3$)$_2$φ | NH | H | H | 2 | COCH$_2$Cl | 119–125 | 57.4 | 56.5 | 5.9 | 6.0 | 19.1 | 18.1 |
| 14A | 2,6-(CH$_3$)$_2$φ | NCH$_3$ | SCH$_3$ | H | 1 | H | 101–102 | 54.5 | 55.7 | 6.9 | 7.1 | 21.4 | 20.6 |
| 14B | 2,6-(CH$_3$)$_2$φ | NCH$_3$ | SCH$_3$ | H | 1 | COCH$_2$Cl | 145–147 | 53.2 | 53.9 | 5.7 | 5.8 | 16.5 | 16.9 |
| 15A | 2-CH$_3$—6-C$_2$H$_5$—φ | NH | C$_2$H$_5$ | H | 1 | H | 69–74 | 68.8 | 68.3 | 8.3 | 8.4 | 22.4 | 20.8 |
| 15B | 2-CH$_3$—6-C$_2$H$_5$—φ | NH | C$_2$H$_5$ | H | 1 | COCH$_2$Cl | 101–105 | 59.9 | 57.8 | 6.6 | 6.9 | 17.5 | 15.9 |
| 16A | 2-CH$_3$—6-C$_2$H$_5$—φ | NH | i-C$_3$H$_7$ | H | 1 | H | 89–90 | 69.7 | 69.5 | 8.6 | 8.4 | 21.9 | 20.9 |

TABLE I-continued

Compounds of the formula

Ar—N(R⁵)—(CH₂)ₙC(R³)=N—N=C(R²)—Y (structure with heterocyclic ring)

| No. | Ar | Y | R² | R³ | n | R⁵ | m.p., °C. | C Calc. | C Found | H Calc. | H Found | N(Cl) Calc. | N(Cl) Found |
|---|---|---|---|---|---|---|---|---|---|---|---|---|---|
| 16B | 2-CH₃—6-C₂H₅—φ | NH | i-C₃H₇ | H | 1 | COCH₂Cl | 83–85 | 61.0 | 60.8 | 6.9 | 6.9 | 16.7 | 16.7 |
| 17A | 2-CH₃—6-C₂H₅—φ | NH | H | H | 1 | H | 122–124 | 66.6 | 66.6 | 7.5 | 7.6 | 26.0 | 26.4 |
| 17B | 2-CH₃—6-C₂H₅—φ | NH | H | H | 1 | COCH₂Cl | 153–155 | 57.4 | 53.8 | 5.9 | 5.8 | 19.1 | 17.7 |
| 18A | 2,6-(CH₃)₂φ | NH | SH | H | 1 | H | 224–225 | 56.4 | 55.9 | 6.0 | 6.0 | 23.9 | 23.8 |
| 18B | 2,6-(CH₃)₂φ | NH | SH | H | 1 | COCH₂Cl | 135–137 | 51.8 | 54.7 | 5.3 | 5.4 | 17.3 | 17.4 |
| 19 | 2-CH₃—6-C₂H₅—φ | NCH₃ | SH | H | 1 | H | 139–141 | 59.5 | 59.3 | 6.9 | 6.9 | 21.4 | 21.6 |
| 20A | 2,6-(C₂H₅)₂—φ | NH | H | H | 1 | H | 160–161 | 67.8 | 67.7 | 7.9 | 8.0 | 24.3 | 25.0 |
| 20B | 2,6-(C₂H₅)₂—φ | NH | H | H | 1 | COCH₂Cl | 160–162 | 58.7 | 57.0 | 6.2 | 6.2 | 18.3 | 17.8 |
| 21A | 2-CH₃—6-C₂H₅—φ | NCH₃ | SCH₃ | H | 1 | H | 93–95 | | | | | 11.6(S) | 12.0 |
| 21B | 2-CH₃—6-C₂H₅—φ | NCH₃ | SCH₃ | H | 1 | COCH₂Cl | 92–96 | 54.5 | 56.3 | 6.0 | 6.3 | 15.9 | 17.3 |
| 22A | 2-Cl—6-CH₃—φ | NH | CH₃ | H | 1 | H | 127–128 | 56.3 | 54.4 | 4.7 | 5.8 | 23.9 | 25.1 |
| 22B | 2-Cl—6-CH₃—φ | NH | CH₃ | H | 1 | COCH₂Cl | 162–163 | 49.9 | 49.8 | 4.5 | 4.4 | 17.9 | 18.7 |
| 23A | 2,6-(C₂H₅)₂—φ | NCH₃ | SCH₃ | H | 1 | H | 80–81 | 62.0 | 61.9 | 7.6 | 7.9 | 19.3 | 20.7 |
| 23B | 2,6-(C₂H₅)₂—φ | NCH₃ | SCH₃ | H | 1 | COCH₂Cl | 125–126 | 55.7 | 56.9 | 6.8 | 6.6 | 15.2 | 16.1 |
| 24A | 2,6-(CH₃)₂φ | O | SCH₃ | H | 1 | H | 84–85 | 57.8 | 57.5 | 6.1 | 6.2 | 16.9 | 17.3 |
| 24B | 2,6-(CH₃)₂φ | O | SCH₃ | H | 1 | COCH₂Cl | 111–115 | 51.6 | 52.8 | 5.0 | 5.2 | 12.9 | 13.8 |
| 25A | 2-CH₃—φ | NH | CH₃ | H | 1 | H | 117–118 | 65.3 | 62.6 | 7.0 | 7.4 | 27.7 | 32.2 |
| 25B | 2-CH₃—φ | NH | CH₃ | H | 1 | COCH₂Cl | 118–122 | 56.0 | 55.7 | 5.4 | 5.6 | 20.1 | 20.5 |
| 26A | 3-CF₃—φ | NH | CH₃ | H | 1 | H | 128–129 | 51.6 | 52.6 | 4.3 | 4.5 | 21.8 | 23.6 |
| 26B | 3-CF₃—φ | NH | CH₃ | H | 1 | COCH₂Cl | 111–113 | 46.9 | 47.9 | 3.6 | 3.9 | 16.8 | 17.9 |
| 27A | 3,4-Cl₂—φ | NH | CH₃ | H | 1 | H | 144–145 | 46.7 | 47.6 | 3.9 | 4.2 | 21.8 | 23.3 |
| 27B | 3,4-Cl₂—φ | NH | CH₃ | H | 1 | COCH₂Cl | 53–63 | 43.2 | 41.8 | 3.3 | 3.7 | 16.8 | 17.0 |
| 28 | 2-CH₃—6-C₂H₅—φ | NH | —CH₂CH=CH₂* | H | 1 | COCH₂Cl | 119–120 | 61.4 | 61.8 | 6.4 | 6.5 | 16.8 | 17.8 |
| 29A | 2,6-(CH₃)₂φ | S | CH₃ | H | 1 | H | 68–69 | 61.8 | 62.4 | 6.5 | 6.7 | 18.0 | 18.9 |
| 29B | 2,6-(CH₃)₂φ | S | CH₃ | H | 1 | COCH₂Cl | 117–118 | 54.3 | 54.9 | 5.2 | 5.4 | 13.6 | 14.0 |
| 30 | 2,6-(C₂H₅)₂—φ | NH | —CH₂CH=CH₂ | H | 1 | COCH₂Cl | 123–124 | 62.32 | 63.63 | 6.7 | 6.8 | 16.2 | 18.6 |
| 31 | 2,6-(CH₃)₂φ | NH | —CH₂CH=CH₂ | H | 1 | COCH₂Cl | 144–146 | 60.3 | 60.1 | 6.0 | 6.2 | 17.6 | 18.6 |
| 32 | 2,6-(CH₃)₂φ | NCH₃ | S—i-C₃H₇ | H | 1 | COCH₂Cl | 99–100 | 55.7 | 55.9 | 6.3 | 6.3 | 15.3 | 15.9 |
| 33A | 2,6-(CH₃)₂φ | NH | n-C₅H₁₁ | H | 1 | H | 110–111 | 70.6 | 72.1 | 8.9 | 9.1 | 20.6 | 21.6 |
| 33B | 2,6-(CH₃)₂φ | NH | n-C₅H₁₁ | H | 1 | COCH₂Cl | 102–103 | 62.0 | 59.6 | 7.2 | 6.9 | 16.1 | 16.2 |
| 34A | 2,6-(CH₃)₂φ | NCH₃ | SCH₂C≡CH | H | 1 | H | 106–107 | 62.9 | 62.6 | 6.3 | 6.5 | 19.6 | 20.1 |
| 34B | 2,6-(CH₃)₂φ | NCH₃ | SCH₂C≡CH | H | 1 | COCH₂Cl | 78–80 | 56.3 | 56.7 | 5.2 | 5.4 | 15.4 | 16.0 |
| 35 | 2,6-(CH₃)₂φ | NCH₃ | SCH₂C≡CH₂ | H | 1 | COCH₂Cl | 95–97 | 56.0 | 56.3 | 5.8 | 6.0 | 15.4 | 15.8 |
| 36A | 2,6-(CH₃)₂φ | NH | φ | H | 1 | H | | 73.4 | 73.6 | 6.5 | 7.1 | 20.1 | 19.9 |
| 36B | 2,6-(CH₃)₂φ | NH | φ | H | 1 | COCH₂Cl | 122–127 | 64.3 | 64.4 | 5.4 | 5.7 | 15.8 | 16.2 |

φ represents phenyl
* —CH₂CH=CH₂ and CH=CH—CH₃ mixture

TABLE II

Herbicidal Effectiveness
% Control Pre/Post[1]

| No. | L | M | P | C | W | O |
|---|---|---|---|---|---|---|
| 1A | 0/0 | 0/0 | 0/0 | 0/0 | 0/0 | 0/0 |
| 1B | 50/0 | 45/0 | 87/0 | 100/0 | 100/0 | 90/0 |
| 2A | 0/0 | 0/0 | 0/0 | 0/0 | 0/0 | 0/0 |
| 2B | 98/50 | 75/25 | 88/32 | 100/20 | 100/75 | 100/30 |
| 3 | 0/0 | 0/0 | 0/0 | 0/0 | 0/0 | 0/0 |
| 4 | 10/0 | 10/0 | 65/0 | 100/20 | 100/60 | 93/50 |
| 5A | 0/0 | 0/0 | 0/0 | 0/0 | 0/0 | 0/0 |
| 5B[2] | — | — | — | — | 100/— | — |
| 6A | 0/0 | 0/0 | 0/0 | 0/0 | 0/0 | 0/0 |
| 6B[2] | — | — | — | — | — | 100/— |
| 7A | 0/0 | 0/0 | 0/0 | 0/0 | 0/0 | 0/0 |
| 7B[3] | 0/0 | 0/0 | 0/0 | 0/0 | 0/0 | 0/0 |
| 8A | 0/0 | 0/0 | 0/0 | 0/0 | 0/0 | 0/0 |
| 8B[2] | 100/— | 83/— | 90/— | 100/— | 100/— | 99/— |
| 9A | 0/0 | 0/0 | 0/0 | 0/0 | 0/0 | 0/0 |
| 9B | 100/25 | 55/25 | 100/0 | 100/70 | 100/75 | 100/65 |
| 10A | 0/0 | 0/0 | 0/0 | 0/0 | 0/0 | 0/0 |
| 10B | 0/25 | 0/35 | 0/0 | 80/40 | 95/55 | 15/25 |
| 11A | 0/0 | 0/0 | 0/0 | 0/0 | 0/0 | 0/0 |
| 11B | 100/25 | 80/20 | 90/20 | 100/55 | 100/73 | 97/10 |
| 12A | 0/0 | 0/0 | 0/0 | 0/0 | 0/0 | 0/0 |
| 12B | 75/45 | 75/0 | 90/20 | 100/65 | 100/80 | 97/45 |
| 13 | 75/0 | 20/0 | 40/0 | 85/60 | 97/63 | 25/20 |
| 14A | 0/0 | 0/0 | 0/0 | 0/0 | 0/0 | 0/0 |

TABLE II-continued

Herbicidal Effectiveness
% Control Pre/Post[1]

| No. | L | M | P | C | W | O |
|---|---|---|---|---|---|---|
| 14B | 0/0 | 0/0 | 0/0 | 90/0 | 100/0 | 10/0 |
| 15A | 0/0 | 0/0 | 0/0 | 0/0 | 0/0 | 0/0 |
| 15B | 100/35 | 100/35 | 100/30 | 100/75 | 100/80 | 100/55 |
| 16A | 0/0 | 0/0 | 0/0 | 0/0 | 0/0 | 0/0 |
| 16B | 100/35 | 95/40 | 95/40 | 100/70 | 100/75 | 100/70 |
| 17A | 0/0 | 0/0 | 0/0 | 0/0 | 0/0 | 0/0 |
| 17B | 100/65 | 90/75 | 95/65 | 100/75 | 100/75 | 100/60 |
| 18A | 0/0 | 0/0 | 0/0 | 0/0 | 0/0 | 0/0 |
| 18B | 0/0 | 0/0 | 0/0 | 0/0 | 0/0 | 0/0 |
| 19 | 0/0 | 0/0 | 0/0 | 0/0 | 0/0 | 0/0 |
| 20A | 0/0 | 0/0 | 0/0 | 0/0 | 0/0 | 0/0 |
| 20B | 97/25 | 95/30 | 100/35 | 95/30 | 100/55 | 97/0 |
| 21A | 0/0 | 0/0 | 0/0 | 0/0 | 0/0 | 0/0 |
| 21B | 0/0 | 0/0 | 0/0 | 0/0 | 98/0 | 0/0 |
| 22A | 0/0 | 0/0 | 0/0 | 0/0 | 0/0 | 0/0 |
| 22B | 85/20 | 80/25 | 93/75 | 100/0 | 100/60 | 95/0 |
| 23A | 0/0 | 0/0 | 0/0 | 0/0 | 0/0 | 0/0 |
| 23B | 0/0 | 0/0 | 0/0 | 0/0 | 0/0 | 0/0 |
| 24A | 0/0 | 0/0 | 0/0 | 0/0 | 0/0 | 0/0 |
| 24B | 10/0 | 10/0 | 10/0 | 100/0 | 100/0 | 85/0 |
| 25A | 0/0 | 0/0 | 0/0 | 0/0 | 0/0 | 0/0 |
| 25B | 100/0 | 45/0 | 70/0 | 97/0 | 100/40 | 0/0 |
| 26B | 10/0 | 10/0 | 0/0 | 0/0 | 65/0 | 0/0 |
| 27A | 0/0 | 0/0 | 0/0 | 0/0 | 0/0 | 0/0 |
| 27B | 0/0 | 0/0 | 0/0 | 0/0 | 0/0 | 0/0 |
| 28 | 100/0 | 93/0 | 100/0 | 100/0 | 100/0 | 97/0 |

[1] 33 micrograms per cm$^2$
[2] 11 micrograms per cm$^2$
[3] 1.8 micrograms per cm$^2$
L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
C = Wild Oats (*Avena fatua*)

What is claimed is:

1. A compound of the formula $$\text{Ar-N} \begin{array}{c} \text{C(=O)-R}^1 \\ \text{(CH)}_n\text{-C(=N)-Y-C(=N)-R}^2 \\ | \\ \text{R}^3 \end{array}$$

wherein Ar is 2,6-disubstituted phenyl substituted with the same or different substituents selected from fluoro, chloro, bromo, iodo, alkyl of 1 to 4 carbon atoms, alkoxy of 1 to 4 carbon atoms or haloalkyl of 1 to 4 carbon atoms and 1 to 3 of the same or different halogens selected from fluoro, chloro, bromo or iodo, $R^1$ is halomethyl of 1 to 3 of the same or different halogens selected from fluoro, chloro, bromo, or iodo, $R^2$ is hydrogen; alkyl of 1 to 6 carbon atoms; alkenyl of 2 to 6 carbon atoms; alkynyl of 2 to 6 carbon atoms; cycloalkyl of 3 to 6 carbon atoms; or haloalkyl of 1 to 4 carbon atoms and 1 to 3 of the same or different halogens selected from fluoro, chloro, bromo or iodo; alkoxy of 1 to 6 carbon atoms; alkylthio of 1 to 6 carbon atoms; alkenylthio of 2 to 6 carbon atoms; alkynylthio of 2 to 6 carbon atoms; phenyl; phenyl substituted with 1 to 3 of the same or different substituents selected from fluoro, chloro, bromo, iodo, alkyl of 1 to 4 carbon atoms, alkoxy of 1 to 4 carbon atoms or haloalkyl of 1 to 4 carbon atoms and 1 to 3 of the same or different halogens selected from fluoro, chloro, bromo or iodo; or $NR^5R^6$ wherein $R^5$ and $R^6$ individually are hydrogen, alkyl of 1 to 6 carbon atoms, alkenyl of 2 to 6 carbon atoms or alkynyl of 2 to 6 carbon atoms, $R^3$ is hydrogen or alkyl of 1 to 6 carbon atoms, n is 1 or 2, and Y is O or S.

2. A compound of the formula defined in claim 1 wherein Y is O.

3. A compound of the formula defined in claim 1 wherein Y is sulfur.

4. An herbicidal composition comprising an herbicidally effective amount of the compound defined in claim 1 and a biologically inert carrier.

5. A method for controlling undesirable vegetation which comprises applying to said vegetation or its growth medium an herbicidally effective amount of the compound defined in claim 1.

6. The compound of claim 1 wherein said disubstituted phenyl substituents are independently selected from the group consisting of fluoro, chloro, bromo, alkyl having 1-4 carbon atoms and alkoxy having 1-4 carbon atoms.

7. The compound of claim 6 wherein said disubstituted phenyl substituents are independently selected from the group consisting of fluoro, chloro, bromo and alkyl having 1-3 carbon atoms.

8. The compound of claim 7 wherein said disubstituted phenyl substituents are independently selected from the group consisting of alkyl having 1-3 carbon atoms.

9. The compund of claim 1 wherein $R^1$ is monohalomethyl.

10. The compound of claim 8 wherein $R^1$ is monohalomethyl.

11. The compound of claim 1 wherein $R^2$ is hydrogen, alkyl having 1-3 carbon atoms, phenyl, or phenyl substituted with 1 to 3 substituents independently selected from the group consisting of fluoro, chloro, bromo and alkyl having 1-3 carbon atoms.

12. The compound of claim 11 wherein $R^2$ is hydrogen or alkyl having 1-3 carbon atoms.

13. The compound of claim 1 wherein Ar is a 2,6-disubstituted phenyl wherein said substituents are independently selected from the group consisting of alkyl having 1-4 carbon atoms; $R^1$ is chloromethyl or bromomethyl; $R^2$ is hydrogen or alkyl having 1 to 6 carbon atoms; Y is O and n is 1.

14. A compound having the formula:

$$\text{Ar-N(H)-CH(R}^3\text{)-}\underset{\text{Y}}{\text{[oxadiazole ring with R}^2\text{]}}$$

wherein
Ar is phenyl substituted with 1 to 3 of the same or different substituents selected from fluoro, chloro, bromo, or alkyl of 1 to 3 carbon atoms;
$R^2$ is hydrogen; alkyl of 1 to 6 carbon atoms; or haloalkyl of 1 to 4 carbon atoms and 1 to 3 of the same or different halogens selected from fluoro, chloro, bromo or iodo;
$R^3$ is hydrogen or alkyl of 1 to 6 carbon atoms; and
Y is O, or NR wherein R is hydrogen, alkyl of 1 to 6 carbon atoms, alkenyl of 2 to 6 carbon atoms or alkynyl of 2 to 6 carbon atoms.

15. The compound of claim 14 wherein said compound is 2,6-dimethyl-N-[2-methyl-1,3,4-oxadiazol-5-yl)methyl]-aniline.

16. The compound of claim 14 wherein:

$R^2$ is hydrogen, or alkyl of 1 to 6 carbon atoms.

17. The compound of claim 14 wherein Y is oxygen.
18. The compound of claim 14 wherein Y is >NR.
19. The compound of claim 14 wherein $R^3$ is hydrogen.
20. The compound of claim 14 wherein $R^3$ is alkyl of 1 to 6 carbon atoms.
21. The compound of claim 14 wherein $R^2$ is hydrogen.
22. The compound of claim 14 wherein $R^2$ is hydrogen, alkyl of 1 to 3 carbon atoms or haloalkyl having 1 to 4 carbon atoms and 1 to 3 halogens independently selected from fluoro, chloro, bromo, or iodo.
23. The compound of claim 14 wherein Ar is phenyl substituted with 1 or 2 of said substituents.
24. The compound of claim 14 wherein Ar is phenyl substituted with only one of said substituents.
25. The compound of claim 18 wherein Y is >NH.
26. The compound of claim 18 wherein R is hydrogen or alkyl of 1 to 3 carbon atoms.
27. The compound of claim 18 wherein Ar is substituted phenyl having 1 to 3 of the same or different alkyl substituents having 1 to 3 carbon atoms.

* * * * *